(12) United States Patent
Bayon et al.

(10) Patent No.: US 8,198,087 B2
(45) Date of Patent: Jun. 12, 2012

(54) TISSUE ENGINEERING SUPPORT

(75) Inventors: Yves Bayon, Lyons (FR); Philippe Gravagna, Irigny (FR); Alfredo Meneghin, Lyons (FR); Michel Therin, Lyons (FR); Olivier Lefranc, Chatillon sur Chalaronne (FR)

(73) Assignee: Sofradim Production SAS, Trevoux (FR)

( * ) Notice: Subject to any disclaimer, the term of this patent is extended or adjusted under 35 U.S.C. 154(b) by 1121 days.

(21) Appl. No.: 11/881,839

(22) Filed: Jul. 30, 2007

(65) Prior Publication Data

US 2009/0035858 A1 Feb. 5, 2009

(51) Int. Cl.
*C12N 5/00* (2006.01)

(52) U.S. Cl. ........ 435/402; 435/395; 424/426; 424/484; 424/486; 424/93.7

(58) Field of Classification Search .................. None
See application file for complete search history.

(56) References Cited

U.S. PATENT DOCUMENTS

| | | | |
|---|---|---|---|
| 4,970,298 | A | 11/1990 | Silver et al. |
| 5,891,558 | A | 4/1999 | Bell et al. |
| 6,153,292 | A | 11/2000 | Bell et al. |
| 6,262,332 | B1 | 7/2001 | Ketharanathan |
| 6,264,702 | B1 | 7/2001 | Ory et al. |
| 6,391,939 | B2 | 5/2002 | Tayot et al. |
| 6,443,964 | B1 | 9/2002 | Ory |
| 6,451,032 | B1 | 9/2002 | Ory |
| 6,576,019 | B1 | 6/2003 | Atala |
| 6,596,304 | B1 | 7/2003 | Bayon et al. |
| 6,599,323 | B2 | 7/2003 | Melican et al. |
| 6,790,454 | B1 | 9/2004 | Abdul Malak et al. |
| 6,974,679 | B2 | 12/2005 | Andre et al. |
| 2002/0120291 | A1 | 8/2002 | Shalaby |
| 2003/0119985 | A1 | 6/2003 | Sehl et al. |
| 2003/0225355 | A1 | 12/2003 | Butler |
| 2004/0054376 | A1 | 3/2004 | Ory et al. |
| 2004/0132365 | A1 | 7/2004 | Therin et al. |
| 2006/0286144 | A1 | 12/2006 | Yang et al. |
| 2007/0032805 | A1 | 2/2007 | Therin et al. |

FOREIGN PATENT DOCUMENTS

| | | |
|---|---|---|
| EP | 1 216 717 | 6/2002 |
| EP | 1 216 718 | 6/2002 |
| EP | 1 273 312 | 1/2003 |
| EP | 1 535 631 | 6/2005 |
| JP | 11 319 068 | 11/1999 |
| WO | WO 89/08467 | 9/1989 |
| WO | WO 96/08277 | 3/1996 |
| WO | WO99/16381 | 9/1998 |
| WO | WO 99/06079 | 2/1999 |
| WO | WO 00/16821 | 3/2000 |
| WO | WO 2006/138098 | 12/2006 |

OTHER PUBLICATIONS

Nakanishi et al, Journal of Pediatric Surgery, (2003), vol. 38, No. 12, pp. 1781-1784.*
Chen et al, Chemical Communication (2000), pp. 1505-1506.*
A. Hunt et al., Abstract Book, Tissue Engineering & Regenerative Medicine, International Society, European Chapter Meeting 2006, Rotterdam, The Netherlands, Oct. 8-11, 2006, p. 130.
O. Lefranc et al., Urothelial Cell Proliferation on Novel 3D Collagen-Plla Composites for Urological Tissue Engineering, 1 page, 20th European Conf. on Biomaterials, Sep. 27-Oct. 1, 2006. Nantes, France.
O. Lefranc, Enhancement of Smooth Muscle Cell Proliferation in Novel PLLA-Collagen Meshes for Tissue Engineering, 1 page, 20th European Conf. on Biomaterials, Sep. 27-Oct. 1, 2006, Nantes, France.
International Search Report from International Application No. PCT/IB2008/002894 dated Nov. 11, 2009.
Friess, Eur. J. Pharm. Biopharm., 45, 1998.
Laquerriere, J. Neurosurg., 78, 1993.
Gunatillake, et al., Eur. Cells and Mat., vol. 5, 2003.

* cited by examiner

*Primary Examiner* — Allison Ford
(74) *Attorney, Agent, or Firm* — Carter, DeLuca, Farrell & Schmidt, LLP

(57) ABSTRACT

Cell cultures or tissue engineering supports, include at least a porous matrix based on a collagen sponge which defines first pores and a porous three-dimensional knit which defines second pores, the porous matrix filling the three-dimensional knit and all the first and second pores being at least partially interconnected with one another.

42 Claims, 6 Drawing Sheets

B5 B6

B2 B1

B4 B3

B4 B3

TISSUE ENGINEERING SUPPORT

TECHNICAL FIELD

The present disclosure relates to a collagen-based cell culture or tissue engineering support for culturing live cells. The support according to the present disclosure can also be used firstly in vitro for culturing cells and then, secondly, can be implanted into the human body, for example as a wall reinforcement implant that can be used, for example, in the treatment of hernias or for the reconstruction of a wall, for example a visceral wall.

BACKGROUND

Tissue engineering supports are substrates capable of promoting the culture of live cells. These supports are used, for example, in the fields of pharmacy and diagnosis, or alternatively for cell preparation steps.

Collagen-based tissue engineering supports are known. In fact, it is known that collagen constitutes a particularly effective substrate for culturing live cells.

However, in order to effectively promote the culturing of the cells and the proliferation of the latter, it is particularly important for the structure of the support to have a porosity that is able to allow the cells to invade virtually the entire volume formed by the support.

Thus, there remains the need for an optionally bioresorbable tissue engineering support which has a specific porosity that allows effective cell growth.

SUMMARY

The present disclosure aims to remedy this need by providing a tissue engineering support that includes at least:
- an optionally bioresorbable porous matrix based on a collagen sponge which defines first pores,
- an optionally bioresorbable porous three-dimensional knit which defines second pores,
- the porous matrix filling the three-dimensional knit, and all the first and second pores being at least partially interconnected with one another.

The term "tissue engineering" is understood to mean the definition as given by the National Science Foundation (Lake Tahoe, USA, 1988), i.e. the application of the principles and of the methods of engineering and the life sciences aimed at i) understanding the relationships between the structure and function of normal and pathological tissues, and ii) the development of biological substitutes for restoring, maintaining or improving the functions.

When considering tissue engineering in its broadest definition, these biological substitutes are obtained i) either by the in vitro culturing of supports/matrices with cells, ii) or by the implantation of supports/matrices which will generate a biological substitute in vivo, after tissue integration and cell colonisation of the supports/matrices.

For the purpose of the present application, the term "porous" is intended to mean the characteristic according to which a structure exhibits pores, or alternatively gaps, alveoli, holes or orifices, which are open, which may or may not be evenly distributed, and which promote all cell colonisation.

For the purpose of the present application, the term "sponge" is intended to mean a porous structure with pores which may or may not be interconnected, obtained in particular by lyophilization of a solution or suspension.

For the purpose of the present application, the term "collagen" is intended to mean any known collagen of porcine, bovine or human origin, for example natural collagen, esterified collagen, for example methylated, ethylated or alternatively succinylated collagen, or one of its derivatives, which may or may not be heated, which may or may not be oxidized, or alternatively, for example, which is crosslinked with another compound.

For the purpose of the present application, the term "natural collagen" is intended to mean collagen which has not been chemically modified, other than a possible treatment with pepsin in order to digest the telomeric peptides.

For the purpose of the present application, the term "three-dimensional knit" is intended to mean an assembly or arrangement of monofilament or multifilament yarns, obtained by knitting and having a significant thickness, in embodiments of greater than or equal to 0.5 mm. In embodiments, the yarns of the three-dimensional knit are biocompatible.

For the purpose of the present application, the term "interconnected pores" is intended to mean open pores which are connected to one another and communicate with one another over the support as a whole, without partitioning, such that a cell that is in a pore can pass from one pore to the other, over the entire support, and can in theory circulate through all the pores of the support. For the purpose of the present application, the expression "pores which are at least partially interconnected" is intended to mean that certain pores, for example from 0.1% to 80% of all the pores, may be closed and not communicate with the adjacent pores. Thus, the support according to the present disclosure may be such that all of its pores, i.e. the first and the second pores, are all completely interconnected. In other embodiments of the present disclosure, the support according to the present disclosure may be such that all of its pores, i.e. the first and the second pores, are partially interconnected, i.e. certain pores are closed to communication with the adjacent pores.

For the purpose of the present application, the term "interconnectivity" is intended to mean the ability of the support to allow any cell that is in a pore to circulate within all the other pores of the support. Thus, in the case of complete interconnectivity, all the pores of the support are accessible to any cell seeded onto the support.

The support according to the present disclosure, in particular due to its specific porosity, which permits at least an interconnectivity of all the first and second pores, allows particularly efficient culturing of live cells. Thus, the live cells seeded onto the supports according to the present disclosure exhibit good adhesion on these supports and a satisfactory rate of proliferation in these supports. Thus, a three-dimensional colonisation of the supports according to the present disclosure by the live cells can be obtained within days following seeding, for example in less than four days. Confluence of the live cells seeded onto the supports according to the present disclosure can be obtained within two weeks of culturing following seeding. Moreover, the phenotype of the cells cultured on the supports according to the present disclosure is conserved during the culture period. The cells seeded onto the supports according to the present disclosure spread out and proliferate on the yarns of the three-dimensional knit and in the pores of the supports according to the present disclosure.

Stem cells seeded onto the supports according to the present disclosure conserve their differentiation potential.

In embodiments, the porous collagen sponge matrix is bioresorbable.

In the present application, the term "bioresorbable" is intended to mean the characteristic according to which a material is absorbed by the biological tissues and disappears in vivo after a given period, which can range, for example, from one day to several months, depending on the chemical nature of the material.

In one embodiment of the present disclosure, the three-dimensional knit is bioresorbable.

Thus, in particular when the porous matrix and the three-dimensional knit of the support according to the present disclosure are bioresorbable, the support can constitute an implant. In the present application, the term "implant" is intended to mean a biocompatible medical device that can be implanted in the human or animal body. In particular, the support according to the present disclosure can constitute an implant in the form of a wall reinforcement particularly suitable for the treatment of wall defects, for example hernias, and for tissue reconstruction when a permanent reinforcement is not necessary. In fact, due to its three-dimensional porous structure in which all the pores are interconnected, the support according to the present disclosure promotes a gradual, controlled and homogeneous cell growth. Thus, when the support according to the present disclosure is completely bioresorbable, the gradual degradation in vivo of the various elements constituting the support, and in particular of the collagen sponge, allows the pores that were initially closed to open little by little. All the pores, the first and the second pores, become completely interconnected after sufficient partial degradation in vivo after implantation: the cells proliferate and regenerate the tissue at the site of the defective wall. The more the regenerated tissue grows, the more the mechanical strength of the support decreases, subsequent to its gradual degradation. In addition, the cells can freely colonise all the sites of the support by virtue of the interconnectivity of the pores of the sponge matrix and of the pores of the three-dimensional knit: thus, the cell growth is evenly distributed over the entire support, leaving, once the support is completely resorbed, a neotissue reconstructed at the site where the support was initially implanted, i.e. at the site of the original tissue defect.

In embodiments of the support of the present disclosure, the collagen is a mixture of at least one collagen which undergoes slow bioresorption in vivo and at least one collagen which undergoes rapid bioresorption in vivo.

The expression "collagen which undergoes slow bioresorption or bio-degradation in vivo" is intended to mean a collagen that can be completely bioresorbed or degraded in vivo, i.e. within the human body, according to an adaptable and controllable time period ranging from approximately 3 months to 12 months. The expression "collagen which undergoes rapid bioresorption or biodegradation in vivo" is intended to mean a collagen which can be completely bioresorbed or degraded in vivo, i.e. within the human body, according to an adaptable and controllable time period ranging from approximately 1 week to 8 weeks.

In such an embodiment of the present disclosure, the collagen sponge matrix exhibits, once implanted, two-speed resorption kinetics, with a part of its structure which resorbs more rapidly than the other part. Such an embodiment thus makes it possible to create, in vivo, in a gradual and controlled manner, new pores that are interconnected with the already existing pores, that the patient's cells will colonize little by little as the part made of collagen which undergoes rapid bioresorption is degraded. The cell growth will thus gradually take place homogeneously in vivo. Such an embodiment also makes it possible to increase, over time, the interconnectivity of the support according to the present disclosure when it is used as an implant and thus improve the tissue integration of the support.

The collagen which undergoes slow bioresorption in vivo can be chosen from natural collagen, esterified collagen, which may or may not be heated, and mixtures thereof, and more particularly chosen from glutaraldehyde-crosslinked collagen, bifunctional or trifunctional glycidyl ethers, carbodiimides, acyl azides, divinylsulphone and mixtures thereof. It may also be obtained by crosslinking the collagen by means of physical methods such as photooxidation.

The collagen which undergoes rapid bioresorption in vivo may be chosen from natural collagen, esterified collagen, which may or may not be heated, and mixtures thereof, and more particularly chosen from oxidized collagen, glutaraldehyde-crosslinked collagen, bifunctional or trifunctional glycidyl ethers, carbodiimides, acyl azides, divinylsulphone, collagen crosslinked by UV irradiation or by heat treatment, and mixtures thereof.

In embodiments of the present disclosure, the collagen forming the sponge is a mixture of oxidized collagen and glutaraldehyde-crosslinked collagen. It is known that oxidized collagen degrades in vivo and is bioresorbed in a few weeks, whereas glutaraldehyde-crosslinked collagen bioresorbs in several months.

In embodiments of the present disclosure, the three-dimensional knit includes only monofilament and/or multifilament yarns made of bioresorbable material which has an in vivo degradation time ranging from approximately 3 months to 2 years.

In embodiments of the support of the present disclosure, the bioresorbable material may be chosen from poly(lactic acid) (PLA), poly(glycolic acid) (PGA), oxidized cellulose, polycaprolactone (PCL), polydiaxanone (PDO), trimethylene carbonate (TMC), polyvinyl alcohol (PVA), polyhydroxyalkanoates (PHAs), polyamides, polyethers, copolymers thereof and mixtures thereof.

In embodiments of the support of the present disclosure, the second pores have an average diameter ranging from 1 to 5 mm.

In embodiments of the support of the present disclosure, the knit has a two-dimensional porosity of less than or equal to 20%.

For the purpose of the present application, the term "two-dimensional porosity" is intended to mean a porosity calculated from two-dimensional images corresponding to views from above the support according to the present disclosure, these images then being processed by software which analyses them, for instance the Image J software.

In embodiments of the present disclosure, the knit has a three-dimensional porosity of greater than or equal to 90%.

For the purpose of the present application, the term "three-dimensional porosity" is intended to mean a porosity measured in the following way: the dimensions, i.e. length, width and thickness, of the knit, taken alone, are measured; moreover, the density of the yarns used to knit this knit are known. The knit is weighed. By means of a simple subtraction, the volume occupied by the empty spaces within the knit is deduced therefrom. The three-dimensional porosity over the entire knit is determined as being the percentage of empty volume relative to the total volume of the knit.

Thus, the knit of the support according to the present disclosure may advantageously have both a two-dimensional porosity of less than or equal to 20% and a three-dimensional porosity of greater than or equal to 90%. The combination of these porosity values, which may appear to be paradoxical, makes it possible in particular to obtain, with the sponge forming the matrix of the support according to the present disclosure, an interconnectivity for excellent cell proliferation. Thus, when the support according to the present disclosure is manufactured, the collagen forming the sponge of the support matrix has, by virtue of the high three-dimensional porosity of the knit of the support according to the present disclosure, a direct access within the three-dimensional structure and therefore the pores of the knit.

The applicant has also noted that such a dimensional porosity of the three-dimensional knit contributes to forming interconnected pores in the collagen sponge, in all the dimensions of the sponge. Thus, the degree of interconnectivity of the pores of the collagen sponge, i.e. of the first pores, can also be controlled, to a certain extent, by the two-dimensional porosity of the three-dimensional knit, which can be made to vary between 0 and 20%.

In embodiments of the support of the present disclosure, the three-dimensional knit has a thickness ranging from approximately 2 mm to 6 mm, in embodiments ranging from 2 mm to 4 mm.

In embodiments of the present disclosure, the three-dimensional knit includes a first face and a second face, the first face and the second face being opposite and separated from one another by the thickness of the knit, the first face and the second face being connected to one another by a spacer made of monofilament yarns, multifilament yarns or a combination of monofilament yarns and multifilament yarns.

In the present disclosure, the term "spacer" is intended to mean the sheet(s) of yarns which connect(s) the two faces of a three-dimensional fabric to one another, thus constituting the thickness of such a knit.

Such an embodiment of the knit of the support according to the present disclosure, with spacer yarns connecting a first face of the knit to a second face of the knit, contributes to reinforcing the interconnectivity of the pores, and in particular of the first pores, throughout the thickness of the collagen sponge, included in the three-dimensional knit. The interconnectivity of these pores can also be controlled, to a certain extent, by the density of the spacer yarns and their distribution between the two faces of the three-dimensional knit.

In embodiments of the present disclosure, the spacer is made of monofilament yarns.

Such an embodiment of the knit of the support according to the present disclosure, with the spacer made of monofilament yarns, makes it possible to confer excellent mechanical strength on the knit and thus the support according to the present disclosure. In particular, during the optional step of thermosetting the knit, the latter keeps its mechanical properties intact. The support can thus be handled extremely easily. It is thus particularly suitable for use as a tissue engineering support for culturing cells in vitro.

Furthermore, when the support according to the present disclosure is used as an implant, it effectively performs its wall reinforcement functions throughout the entire period required for complete cell colonisation in order to regenerate the tissue at the site of the original tissue defect and in the three-dimensional space provided by the knit.

The first and second faces of the knit can be made of monofilament yarns, multifilament yarns or a combination of monofilament and multifilament yarns.

The monofilament or multifilament yarns used to prepare the first and second faces and the spacer of the three-dimensional knit of the support according to the present disclosure can be chosen from yarns made of material which undergoes slow bioresorption, yarns made of material which undergoes rapid bioresorption, and mixtures thereof.

The expression "yarn made of material which undergoes slow bioresorption" is intended to mean yarn obtained from a material that can be completely bioresorbed or degraded in vivo, i.e. within the human body, according to an adaptable and controllable period of time ranging from approximately 6 months to 2 years.

As an example of a yarn made of material which undergoes slow bioresorption, mention may be made of poly(lactic acid) yarns.

The expression "yarn made of material which undergoes rapid bioresorption" is intended to mean a yarn obtained from a material that can be completely bioresorbed or degraded in vivo, i.e. within the human body, according to an adaptable and controllable period of time ranging from approximately 1 week to 6 months.

As examples of yarns made of material which undergoes rapid bioresorption, mention may be made of poly(glycolic acid) yarns, oxidized cellulose yarns, poly(lactic acid) yarns partially degraded by a treatment such as repeat cycles of gamma-irradiation at doses of greater than or equal to 25 kGy, and mixtures thereof.

In embodiments of the present disclosure, the monofilament yarns which make up the spacer can include only yarns made of material which undergoes slow bioresoprtion, for example of poly(lactic acid). The first and second faces can also be made of a mixture of multifilament yarns made of material which undergoes slow bioresorption, for instance poly(lactic acid), and of multifilament yarns made of material which undergoes rapid bioresorption, for instance of poly (glycolic acid) or oxidized cellulose.

In other embodiments of the support according to the present disclosure, the monofilament yarns which make up the spacer can, for example, include a mixture of yarns which undergo slow bioresorption and yarns which undergo rapid bioresorption. The first and second faces can be made of a mixture of multifilament yarns made of material which undergoes slow bioresorption, for example poly(lactic acid) and of multifilament yarns made of material which undergoes rapid bioresorption, for instance of poly(glycolic acid) or oxidized cellulose.

In embodiments of the support according to the present disclosure, the knit is isoelastic.

For the purpose of the present application, the term "isoelastic knit" is intended to mean a knit which has isotropic elastic mechanical properties, i.e. substantially equivalent in all directions.

In embodiments, the ratio of respective extensions in the warp direction and in the weft direction is between 0.4 and 2.5, at a physiological force of for example 50N for abdominal wall repair.

It has been found, that such an isoelastic knit allows excellent reinforcement of visceral walls: specifically, the knit is deformed and extended in a more homogeneous manner, thus limiting the risk of wall or hernia rupture.

In embodiments of the support of the present disclosure, at least a part of the yarns constituting the three-dimensional knit are coated with a bioresorbable coating. For example, the coating can be chosen from collagen, chitosan, polysaccharides or mixtures thereof. Such a yarn coating makes it possible in particular to eliminate any possible crevice within the knit of the support according to the present disclosure, for example where the yarns cross.

In embodiments of the present disclosure, the support also includes one or more active compounds chosen from antiseptics, anti-inflammatories, growth factors, polysaccharides such as fucans, extracellular matrix proteins such as fibronectin, laminin, elastin, glycosaminoglycans or proteoglycans, and mixtures thereof.

In embodiments of the present disclosure, the support also includes a bioresorbable film on at least one of its faces. The film can include at least collagen. The film can, for example, include oxidized collagen, polyethylene glycol and glycerol. Such a film can advantageously have a smooth anti-adhesive surface.

In embodiments of the present disclosure, the support is seeded with live cells. The specific porosity provided by the structure of the support according to the present disclosure promotes cell proliferation.

The cells may be chosen from the following cells, alone or in any possible combinations thereof: striated muscle cells, smooth muscle cells, endothelial cells, epithelial cells, mesothelial cells, monocytes, fibroblasts, myofibroblasts, and stem cells of each of the above cell types.

In embodiments of the present disclosure, the support is seeded with smooth muscle cells.

In other embodiments, the support according to the present disclosure is seeded with urothelial cells.

In embodiments of the support according to the present disclosure, the collagen sponge is seeded with muscle-type cells and the bioresorbable film is seeded with endothelial or epithelial cells. When such a support according to the present disclosure is then used as an implant and is implanted in vivo, the presence of the endothelial or epithelial cells on the support/implant makes it possible to accelerate, in vivo, the formation of a new endothelium or epithelium.

Alternatively, the collagen sponge is seeded with striated muscle cells and the bioresorbable film is seeded with mesothelial cells. Such a support, when it is then used as an implant and is implanted in vivo, participates in an effective reconstruction of an abdominal wall.

In yet other embodiments of the support according to the present disclosure, the collagen sponge is seeded with smooth muscle cells and the bioresorbable film is seeded with urothelial cells. Such a support, when it is then used as an implant and is implanted in vivo, participates in an effective reconstruction of a bladder wall.

The present disclosure also relates to the use of a support as described above, for culturing live cells.

BRIEF DESCRIPTION OF THE DRAWINGS

The embodiments of the present disclosure will be described more clearly by means of the description which follows and the attached drawings in which.

DETAILED DESCRIPTION

Figure 1:
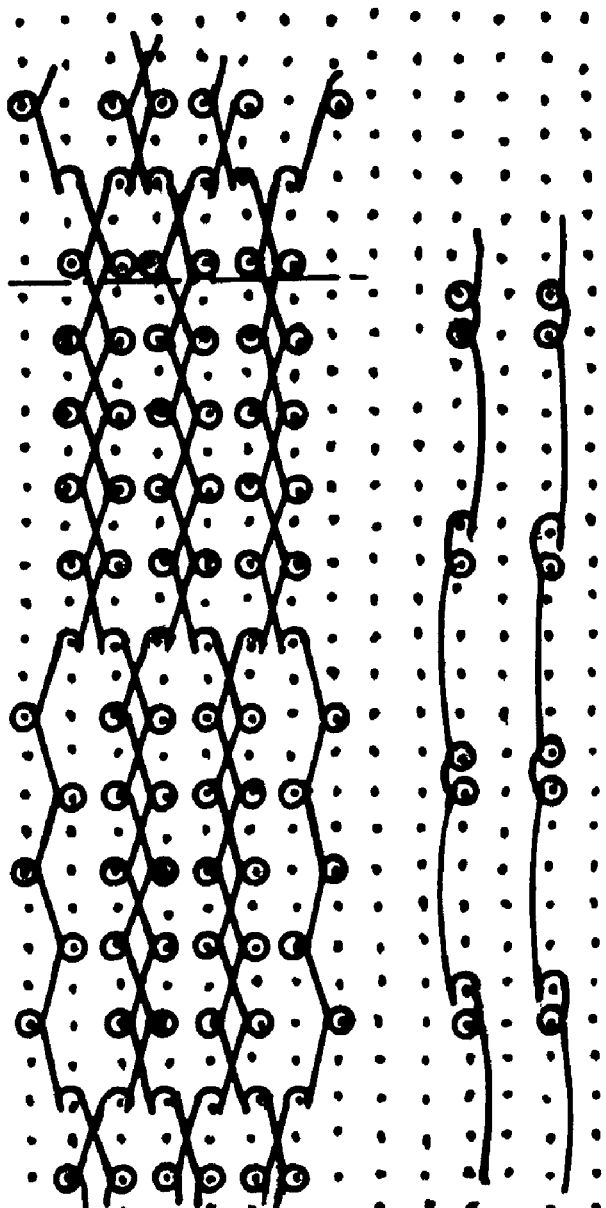
FIGS. 1 to 2B represent patterns of knits suitable for the support according to embodiments of the present disclosure.
Figure 1:
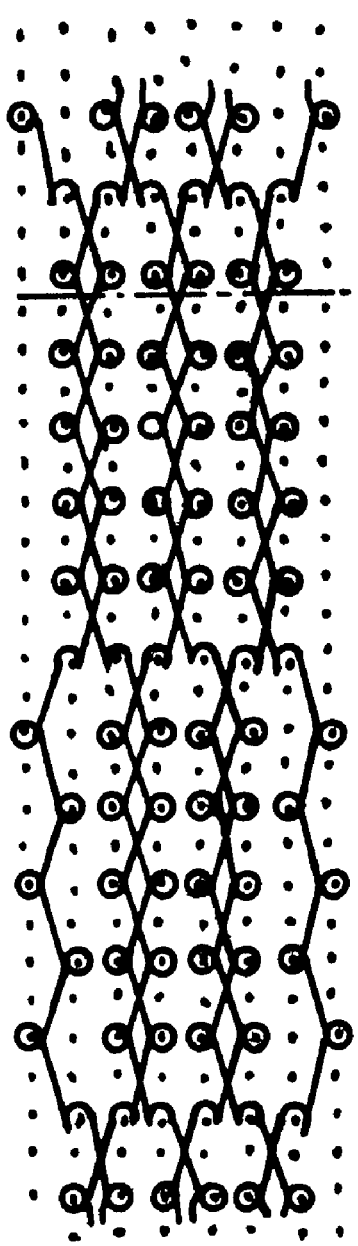

Supports according to the present disclosure include a porous matrix, which can advantageously be bioresorbable, based on a collagen sponge which defines first pores. Such a sponge may be obtained by lyophilization of a collagen suspension. The sponge obtained has pores, or gaps, alveoli, holes or orifices, which may or may not be evenly distributed, and which are more or less interconnected, according to the lyophilization process used. Such lyophilization processes are known. It is known practice to vary the temperature and the rate of freezing and also the characteristics of the collagen solution or suspension to be lyophilized (pH, concentration, etc.) according to the structure of the sponge that it is desired to obtain (see U.S. Pat. No. 4,970,298; Doillon et al, J Biomed Mater Res, 1986; Schoof, J Biomed Mater Res, 2001; O'Brien et al, Biomaterials, 2004).

In embodiments of the support according to the present disclosure, the first pores, defined by the sponge, are homogeneously distributed within the matrix. These first pores can, for example, have an average diameter ranging from 50 to 500 µm. These first pores, defined within the sponge taken alone, in the absence of the knit of the support according to the present disclosure, may or may not be interconnected with one another.

A suitable collagen sponge of the matrix of the support according to the present disclosure may be obtained from a mixture of at least one collagen which undergoes slow bioresorption in vivo and at least one collagen which undergoes rapid bioresorption in vivo.

The collagen which undergoes slow bioresorption in vivo can be chosen from any collagen, which is pure or derived, which may or may not be heated, and which may or may not be oxidized, having a bioresorption or biodegradation time of between 3 and 12 months. For example, the collagen which undergoes slow bioresorption in vivo can be chosen from glutaraldehyde-crosslinked collagen, bifunctional or trifunctional glycidyl ethers, carbodiimides, acyl azides, divinylsulphone and mixtures thereof. It can also be obtained by crosslinking the collagen by means of physical methods such as photooxidation.

In embodiments of the present disclosure, glutaraldehyde-crosslinked collagen is used as collagen which undergoes slow bioresorption in vivo. Such a collagen can, for example, be obtained by incubation of a solution of collagen neutralized with a solution of glutaraldehyde, removal of excess glutaraldehyde and neutralization so as to obtain a glutaraldehyde-crosslinked collagen precipitate.

The collagen which undergoes rapid bioresorption in vivo can be chosen from any collagen, which is pure or derived, which may or may not be heated, and which may or may not be oxidized, having a bioresorption or biodegradation time of between one day and 3 months, in embodiments between one day and 8 days. For example, the collagen which undergoes rapid bioresorption in vivo can be chosen from oxidized collagen, glutaraldehyde-crosslinked collagen, bifunctional or trifunctional glycidyl ethers, carbodiimides, acyl azides, divinylsulphone, collagen crosslinked by UV-beta- or gamma-irradiation or by heat treatment, and mixtures thereof.

In embodiments of the present disclosure, oxidized collagen, for example oxidized with periodic acid, is used as collagen which undergoes rapid bioresorption in vivo. Examples of preparation of oxidized collagen suitable for the present disclosure are described in U.S. Pat. No. 6,596,304.

The collagen used may also be porcine collagen type I, extracted from porcine dermis by solubilization at acidic pH or by digestion with pepsin, and purified by saline precipitations according to known techniques.

Dry collagen fibres, obtained by precipitation of an acidic solution of collagen by adding NaCl, and then washing and drying of the precipitate obtained with aqueous solutions of acetone having an increasing concentration of from 80% to 100%, can be used.

Alternatively, bovine or human collagens I or III, or a mixture thereof in any proportions, can be used.

In the case of human collagens of placental origin, they can be prepared by extraction with pepsin according to the method described in application EP-A0 214 035. The products sold by the company Inamed Corporation (a wholly-owned subsidiary of Allergan, Inc., Irvine, Calif.), under the names VITROGEN® or ZYDERM®, may also be suitable for use in embodiments of the present disclosure.

In one embodiment of the present disclosure, the collagen which forms the sponge is a mixture of oxidized collagen and glutaraldehyde-crosslinked collagen. Thus, a suspension including the oxidized collagen and the glutaraldehyde-crosslinked collagen is prepared. The suspension can include the two collagens in equal concentrations or, on the other hand, predominantly one of the two collagens and a minor amount of the other. The ratio of the concentration of one of the two types of collagen to the other may be between 1 and 5.

Supports according to the present disclosure also include a porous, optionally bioresorbable, three-dimensional knit which defines second pores. This knit can include only monofilament and/or multifilament yarns, which may be made of bioresorbable material. By way of example, the multifilament yarns can have a count ranging from 50 to 110 dtex. Also by way of example, the monofilament yarns can have a diameter ranging from 0.10 to 0.18 mm. In embodiments, the yarns constituting the knit of the support according to the present disclosure have an in vivo resorption or degradation time ranging from approximately 3 months to 2 years.

Thus, the bioresorbable material that can constitute the yarns of the knit of a support according to the present disclosure may be chosen from poly(lactic acid) (PLA), poly(glycolic acid) (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyethers, copolymers thereof and mixtures thereof.

In embodiments of the present disclosure, the three-dimensional knit includes a first face and a second face, opposite and separated from one another by the thickness of the knit. The first and second faces may be connected to one another by a spacer. For example, the spacer may be a sheet of linker yarns. Each face can include one or more sheets of yarns. The yarns constituting each of the two faces and the spacer may be identical or different.

In embodiments of the present disclosure, the first and second faces of the knit are identical. For example, each face is made of two sheets of yarns. In embodiments, the yarns constituting the two faces of the knit are made of multifilament yarns of poly(lactic acid). Such yarns resorb completely in vivo in the space of 6 months to 2 years. Yarns suitable for producing the two faces of the knit of the support according to the present disclosure are, for example, 84 dtex poly(lactic acid) multifilament yarns with 24 filaments per yarn, each filament having a diameter of approximately 18 μm. Alternatively, 83.3 dtex poly(glycolic acid) multifilament yarns with 30 filaments per yarn can also be used.

In embodiments of the present disclosure, the yarns constituting the spacer are monofilament yarns. Such an embodiment makes it possible to confer on the knit a better mechanical strength and a better resistance to thermosetting when the knit is thermoset after the knitting phase. In embodiments, the spacer is made of monofilament yarns of poly(lactic acid). Yarns suitable for preparing the spacer of the knit of implants according to the present disclosure are, for example, 220 dtex poly(lactic acid) monofilament yarns, the monofilament having a diameter of approximately 150 μm.

Examples of a knit suitable for a support according to the present disclosure are described in document EP 0 999 805. The knit of the support according to the present disclosure can be produced on a knitting machine of the Raschel type, for example using 5 or 6 bars.

Figure 2:
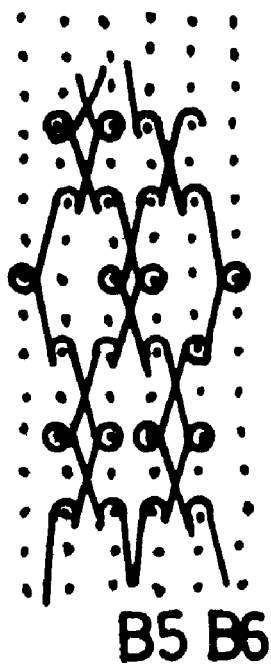
Figure 2:
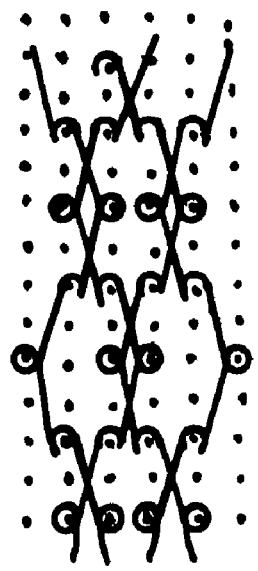

Examples of a pattern suitable for the knit of a support according to the present disclosure are shown in FIGS. 1 and 2.

In these figures, the references B1-B6 represent the bars 1 to 6.

The first face can, for example, be produced with bars 1 and 2. The second face can be produced in the same way, with bars 5 and 6.

Figure 2A:
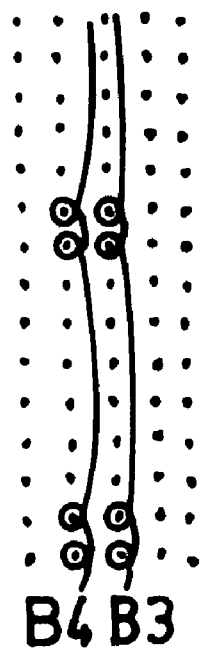
Figure 2B:
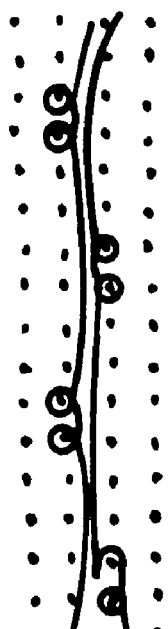

The spacer can be produced with bar 3 (cf. FIG. 1) or bars 3 and 4 (FIGS. 2A and 2B).

A knit of the support according to the present disclosure defines second pores, or alveoli, gaps, holes or orifices. These second pores can advantageously have an average diameter or an average volume ranging from 1 to 5 mm. These second pores are completely interconnected with one another. Thus, the second pores created by the knitting at each face of the knit are connected, via the yarns of the spacer, with the second pores created by the knitting at the spacer. Thus, all the second pores and/or gaps, for instance channels, created by the knitting at each face of the knit and in the thickness of the knit are open, connected to one another and communicate with one another: for example, it is possible for the cell colonization to extend from one pore to the other, over the entire knit of a support according to the present disclosure.

The second pores of the knit of a support according to the present disclosure define, for the knit, a two-dimensional porosity and a three-dimensional porosity.

In the present application, the two-dimensional porosity is calculated from two-dimensional images corresponding to views from above the support according to the present disclosure, these images then being processed by software which analyses them, for instance the Image J software. For example, for a measurement, the density of the knit was determined using a Nikon SMZ 800 binocular microscope with a Nikon DN100 digital camera used in combination with a PC computer. The digital images seen from above the knit were multiplied by a factor of 20 and were then processed by the Image J software in order to determine the density of the knit. Once the digital image is captured by the software, it is processed such that the surface area corresponding to the empty spaces in the knit is subtracted from the total surface area of the image. The two-dimensional porosity is determined as being the percentage corresponding to the rest of the digital image.

In embodiments, the knit of the support according to the present disclosure has a two-dimensional porosity, measured as indicated above, of less than or equal to 20%.

In the present application, the three-dimensional porosity is calculated as follows: the dimensions, i.e. length, width and thickness of the knit, taken alone, are measured; moreover, the density of the yarns used to knit this knit is known. The knit is weighed. The volume occupied by the empty spaces within the knit is deduced therefrom by simple subtraction. The three-dimensional porosity over the knit as a whole is determined as being the percentage of empty volume relative to the total volume of the knit.

In embodiments, the knit of the support according to the present disclosure has a three-dimensional porosity, measured as indicated above, of greater than or equal to 90%.

Thus, in embodiments, the knit of the support according to the present disclosure has both a two-dimensional porosity of less than or equal to 20% and a three-dimensional porosity of greater than or equal to 90%. In fact, during the manufacture of a support according to the present disclosure, the collagen forming the sponge of the matrix of the support has, by virtue of the high three-dimensional porosity of the knit of the support, a direct access within the three-dimensional structure and therefore the pores of the knit. Thus, during the manufacture of the support, and in particular during the lyophilization for obtaining the sponge in which the knit is embedded, as will be explained below, the high porosity of the knit makes it possible to make all the pores, i.e. the first pores due to the sponge and the second pores of the knit, at least partially interconnected with one another.

In embodiments of a support of the present disclosure, the three-dimensional knit has a thickness ranging from approximately 2 mm to 6 mm, in embodiments ranging from 2 mm to 4 mm.

In embodiments of the present disclosure, the knit is isoelastic, i.e. it has isotropic elastic mechanical properties, i.e. substantially equivalent in all directions.

Thus, in embodiments, the knit of the support according to the present disclosure may have a mechanical strength in the longitudinal direction, i.e. in the direction of the warp of the knit, measured according to ISO standard 13934-1 (properties of substances in tensile testing), ranging from 50 to 300 N. In embodiments, the knit of the support according to the present disclosure has a mechanical strength in the transverse direction, i.e. in the direction of the weft of the knit, measured according to ISO standard 13934-1, ranging from 50 to 300 N.

In embodiments, the knit of the support according to the present disclosure has a mechanical strength in the longitudinal direction, i.e. in the direction of the warp of the knit, measured according to ISO standard 13934-1, ranging from 100 to 250 N. In embodiments, the knit of the support according to the present disclosure has a mechanical strength in the transverse direction, i.e. in the direction of the weft of the knit, measured according to ISO standard 13934-1, ranging from 75 to 200 N.

In embodiments, the knit of the support according to the present disclosure has an elongation at 50N in the longitudinal direction, i.e. in the direction of the warp of the knit, measured according to ISO standard ISO 13934-1, ranging from 10% to 50%. In embodiments, the knit of the support according to the present disclosure has an elongation at 50N in the transverse direction, i.e. in the direction of the weft of the knit, measured according to ISO standard 13934-1, ranging from 10% to 50%.

In embodiments, at least part of the yarns constituting the knit are covered with a bioresorbable coating. The bioresorbable coating can be chosen from oxidized collagen, glutaraldehyde-crosslinked collagen, bifunctional or trifunctional glycidyl ethers, carbodiimides, acyl azides, divinylsulphone, collagen crosslinked by UV-, beta- or gamma-irradiation or by heat treatment, and mixtures thereof. The assembly of yarns constituting the knit can be covered with such a coating. For example, the coating is made of collagen. In particular, a collagen chosen from oxidized collagen, glutaraldehyde-crosslinked collagen and mixtures thereof can be used for such a coating.

In embodiments, the yarns of the knit are covered, at least in part by coating the knit in a solution or suspension of collagen, in one step or in several steps. A coating step includes the actual coating of the knit with the collagen and the drying of the knit. The collagen deposited on the yarns can be crosslinked with glutaraldehyde after each application, as many times as the total number of coating cycles. In embodiments, the yarns are covered by carrying out two or three successive coating cycles.

In other embodiments, the bioresorbable coating can be chosen from polysaccharides including hyaluronic acid, alginic acid, polyglucuronic acid, chitosan, starch, soluble cellulose derivatives and mixtures thereof.

In other embodiments, before it is coated with a bioresorbable coating as described above, the knit according to the present disclosure can be subjected to a surface treatment in order to render it more hydrophilic and thus promote the deposition of the collagen and/or the polysaccharides mentioned above on the knit.

The surface treatment can be carried out according to any process known to those skilled in the art.

In order to produce the support according to the present disclosure, the knit as described above is knitted, beforehand, on a knitting machine. This knit is may advantageously be thermoset, for example by being placed in an oven at from 100 to 200° C., for 30 s to 5 minutes, depending on the chemical nature of the yarns used. The knit is then cut to the sizes desired for the support. The thermosetting can also be carried out after the knit has been cut up.

A suspension containing the collagen intended to form the sponge of the matrix is then prepared. For example, this suspension may include a mixture of collagen which undergoes rapid resorption and collagen which undergoes slow resorption. The collagen suspension is then poured over the three-dimensional knit so as to completely cover it. The whole is then lyophilized, for example according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. The vacuum at the end of secondary desiccation, in embodiments, is between 0.005 and 0.2 mbar. The total lyophilization time is from 18 to 72 hours.

The lyophilization makes it possible to obtain a support in which all the pores, i.e. the first pores, formed with the sponge, and the second pores, i.e. those of the three-dimensional knit present prior to the lyophilization, are at least partially interconnected.

Supports according to the present disclosure can also be coated, on at least one of its faces, with a bioresorbable film. Such a film may be a collagen film. In embodiments of the present disclosure, such a film includes oxidized collagen, polyethylene glycol and glycerol.

This bioresorbable film can be applied to one face of a support according to the present disclosure in the following way: a solution, for example of oxidized collagen, polyethylene glycol and glycerol, is prepared and then spread out in order to form a thin sheet on a hydrophobic flat structure, for example on a structure of polyvinyl chloride or polystyrene. The face of the support to be coated can then be applied carefully to the collagen gel. After exposure to ambient temperature and evaporation, a film which coats one face of the support is obtained. It is also possible to coat the two faces of the support with such a film. In embodiments this film resorbs rapidly in vivo, for example in less than 8 days.

Supports according to the present disclosure can be used in vitro as a tissue engineering support for cell culture. Thus, it is possible to seed a support according to the present disclosure with live cells. Such live cells, cultured within the support according to the present disclosure, can secrete growth factors and extracellular matrix, which can have an important role in the repair and/or strengthening of soft tissues. Thus, it is possible to provide a support according to the present disclosure, in vitro, with cells that promote tissue repair, and then to subsequently implant the support into the wall of the soft tissue to be strengthened. The repair is thus accelerated in vivo due to the presence of cells and/or of extracellular matrix promoting regeneration as soon as the support is implanted.

Supports according to the present disclosure can be seeded with cells chosen from the following cells, alone or in any possible combinations thereof: striated muscle cells, smooth muscle cells, endothelial cells, epithelial cells, mesothelial cells, monocytes, fibroblasts, myofibroblasts, and stem cells of each of the above cell types.

For example, it is possible to seed the support described above with striated or smooth muscle cells, with their progenitors, and fibroblasts, in order to obtain effective wall repair.

Moreover, it is also possible to use a support as described above, one face of which is coated with a bioresorbable film: for example, muscle-type cells can be cultured within the sponge of the matrix of the support, while endothelial or epithelial cells are cultured on the bioresorbable film. These endothelial or epithelial cells, after implantation of the support, make it possible to accelerate the formation of a new endothelium or epithelium in vivo.

Similarly, it is possible to carry out effective reconstruction of an abdominal wall by seeding, before implantation, a support according to the present disclosure with mesothelial cells on the film and with striated muscle cells in the sponge.

Similarly, it is possible to carry out effective reconstruction of a bladder wall by seeding, before implantation, a support according to the present disclosure with urothelial cells on the film and with smooth muscle cells in the sponge.

The present disclosure also relates to a method for repairing a wall defect, by implanting a support as described above at the site of the wall defect.

The non-limiting examples which follow illustrate embodiments in accordance with the present disclosure.

Example 1

Preparation of a Knit for the Support

A three-dimensional knit is produced on a double needle-bar Raschel knitting machine, with 5 guide bars. Each of the faces of the knit, i.e. the first face and the second face, is produced with two guide bars. With reference to FIG. 1, the first face is produced with bars B1 and B2, and the second, opposite, face is produced with bars B5 and B6, each bar being threaded one full, one empty, with the following respective charts:

Bar B1: 1-0-1-1/1-2-2-2/2-3-2-2/2-1-2-2/2-3-2-2/2-1-2-2/2-3-2-2/2-1-1-1/1-0-1-1/1-2-1-1/1-0-1-1/1-2-1-1//.

Bar B2: 2-3-2-2/2-1-1-1/1-0-1-1/1-2-1-1/1-0-1-1/1-2-1-1/1-0-1-1/1-2-2-2/2-3-2-2/2-1-2-2/2-3-2-2/2-1-2-2//.

Bar B5: 2-2-2-1/1-1-1-0/1-1-1-2/1-1-1-0/1-1-1-2/1-1-1-0/1-1-1-2/2-2-2-3/2-2-2-1/2-2-2-3/2-2-2-1/2-2-2-3//.

Bar B6: 1-1-1-2/2-2-2-3/2-2-2-1/2-2-2-3/2-2-2-1/2-2-2-3/2-2-2-1/1-1-1-0/1-1-1-2/1-1-1-0/1-1-1-2/1-1-1-0//.

The pattern corresponding to bars 1, 2, 5 and 6 is reproduced in FIG. 1. Such threading and such a pattern result in porous faces. It is possible to adapt the pattern so as to have alveoli or pores on each face, opposite one another or shifted with respect to one another, in order to make the three-dimensional knit more or less transparent.

Bars B1-B2 and B5-B6 which produce the first and second faces of the knit are threaded with 83.3*/24° multifilament yarns (decitex count: 83.3 g per 10 000 m of yarn) of poly (lactic acid). The filament diameter of the multifilament yarns is approximately 18 μm.

Figure 3:
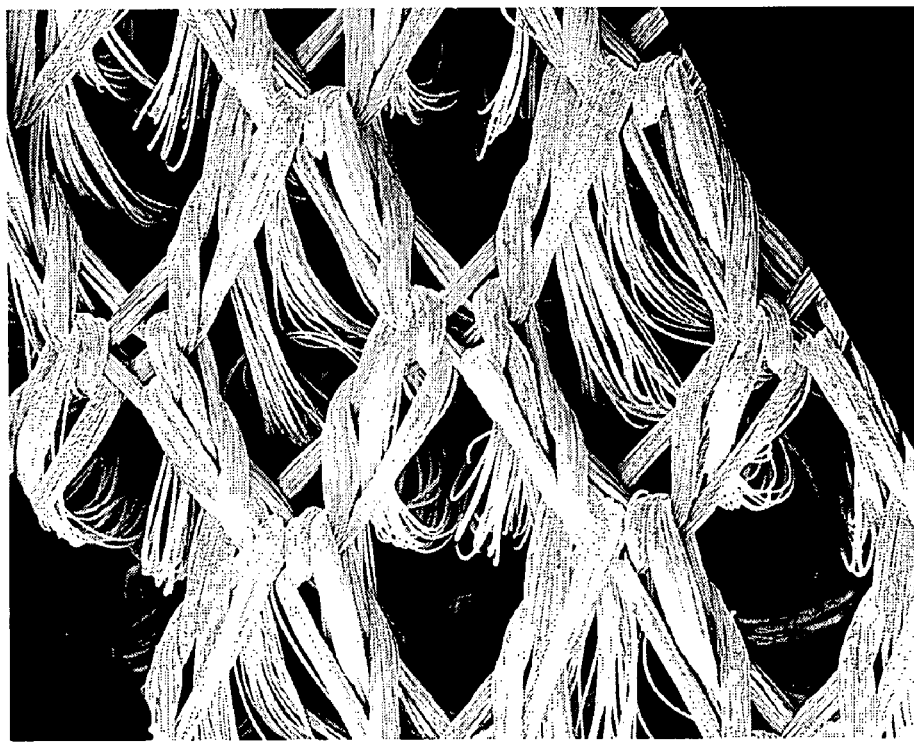
FIGS. 3 and 4 represent scanning electron microscopy images (Hitachi S800 scanning electron microscope with image acquisition and analysis system) of a knit of a support according to the present disclosure, made with multifilament spacer yarns, respectively from the front and from the side.

FIG. 3 represents a scanning electron microscopy image of one face of such a knit.

With reference to FIG. 1, the spacer is produced using bar B3, threaded one full, one empty, according to the following chart:

Bar B3: 0-0-0-0/0-0-0-0/0-1-0-1/1-1-1-1/1-1-1-1/1-0-1-0/1-1-1-1/1-1-1-1/1-0-1-0/0-0-0-0/0-0-0-0/0-1-0-1//.

Bar B3 is threaded with 83.3*/24° multifilament yarns (decitex count: 83.3 g per 10 000 m of yarn) of poly(lactic acid).

The pattern used for the knitting is reproduced in FIG. 1.

Figure 4:

FIG. 4 represents a scanning electron microscopy image of the spacer of such a knit.

The knit is cleaned with methanol-ether and is sterilized by gamma-irradiation.

The knit is thermoset by placing it in an oven at approximately 90° C. for 1 to 5 min.

Such a knit has the following properties, measured as indicated in the present application:

Weight per surface area (g/m²): 165
Pore size: 2.1 mm×1 mm
Thickness: 2.6 mm
Three-dimensional porosity: 95%
Two-dimensional porosity: 4%

This knit is isoelastic. In particular, it has the following mechanical properties:

| Property | Str Wa | Str We | El B Wa | El B We | El Wa 50 N | El We 50 N |
|---|---|---|---|---|---|---|
| Knit Example 1 | 182 | 123 | 69 | 50 | 20 | 22 |

Str Wa: Mechanical Strength in the direction of the warp (in N); calculated according to ISO standard 13934-1
Str We: Mechanical Strength in the direction of the weft (in N); calculated according to ISO standard 13934-1;
El B Wa: Elongation at break in the direction of the warp (as %) calculated according to ISO standard 13934-1;
El B We: Elongation at break in the direction of the weft (as %) calculated according to ISO standard 13934-1;
El Wa 50 N: Elongation at 50 N in the direction of the warp (as %) calculated according to ISO standard 13934-1;
El We 50 N: Elongation at 50 N in the direction of the weft (as %) calculated according to ISO standard 13934-1.

Example 2

Preparation of a Knit for the Support

A knit is prepared in the same way as in Example 1, in which the multifilament yarns of the spacer are replaced with 220 dtex monofilament yarns of poly(lactic acid), with a diameter of approximately 150 μm.

Figure 5:
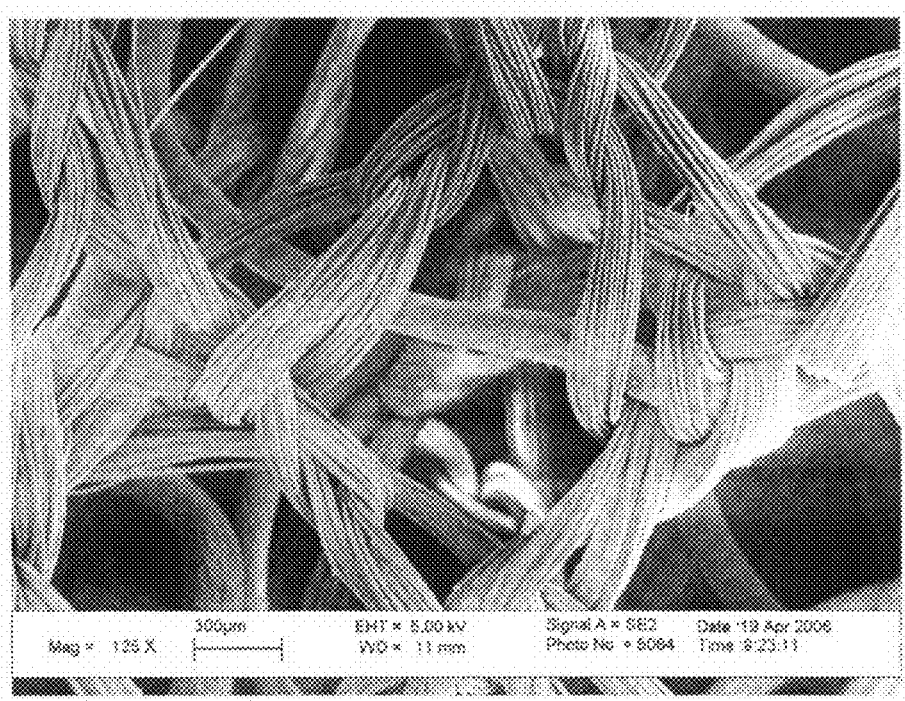
FIG. 5 represents a scanning electron microscopy image (Hitachi S800 scanning electron microscope with image acquisition and analysis system) of a knit of a support according to the embodiments of the present disclosure, made with monofilament spacer yarns.

FIG. 5 represents a scanning electron microscopy image of the spacer of such a knit, prepared with such monofilament yarns.

Such a knit has the following properties, measured as indicated in the present application:
Weight per surface area (g/m$^2$): 104
Pore size: 1.9 mm×1.4 mm
Thickness: 3.3 mm
Three-dimensional porosity: 97.5%
Two-dimensional porosity: 20%

This knit is isoelastic. In particular, it has the following mechanical properties:

| Property | Str Wa | Str We | El B Wa | El B We | El Wa 50 N | El We 50 N |
|---|---|---|---|---|---|---|
| Knit Example 2 | 193 | 82 | 44 | 90 | 11 | 45 |

Str Wa: Mechanical Strength in the direction of the warp (in N); calculated according to ISO standard 13934-1
Str We: Mechanical Strength in the direction of the weft (in N); calculated according to ISO standard 13934-1;
El B Wa: Elongation at break in the direction of the warp (as %) calculated according to ISO standard 13934-1;
El B We: Elongation at break in the direction of the weft (as %) calculated according to ISO standard 13934-1;
El Wa 50 N: Elongation at 50 N in the direction of the warp (as %) calculated according to ISO standard 13934-1;
El We 50 N: Elongation at 50 N in the direction of the weft (as %) calculated according to ISO standard 13934-1.

Example 3

Preparation of a Knit for the Support

A three-dimensional knit is prepared on a double needlebar Raschel knitting machine, with 6 guide bars. Each of the faces of the knit, i.e. the first face and the second face, is prepared with two guide bars. With reference to FIG. 2, the first face is prepared with bars B1 and B2, and the second, opposite, face is prepared with bars B5 and B6, each bar being threaded one full, one empty, with the following respective charts:
Bar B1: 1-0-1-1/1-2-2-2/2-3-2-2/2-1-1-1//.
Bar B2: 2-3-2-2/2-1-1-1/1-0-1-1/1-2-2-2//.
Bar B5: 2-2-2-1/1-1-1-0/1-1-1-2/2-2-2-3//.
Bar B6: 1-1-1-2/2-2-2-3/2-2-2-1/1-1-1-0//.

The pattern corresponding to bars 1, 2, 5 and 6 is reproduced in FIG. 2. Such threading and such a pattern result in porous faces. In this example, the gaps or pores on each face have the following values:
Width: approximately 1 to 1.3 mm
Height: 1.1 to 1.4 mm.

Bars B1-B2 and B5-B6 which produce the first and second faces of the knit are threaded with 83.3 dtex poly(lactic acid) multifilament yarns.

With reference to FIG. 2A, the spacer is prepared using bars B3 and B4, threaded one full, one empty, according to the following respective charts:
Bar B3: 0-1-0-1/0-0-0-0/0-0-0-0/0-0-0-0//.
Bar B4: 0-0-0-0/0-0-0-0/0-1-0-1/0-0-0-0//.

Alternatively, with reference to FIG. 2B, bars B3 and B4 are threaded one full, one empty, according to the following respective charts:
Bar B3: 0-1-0-1/0-0-0-0/0-0-0-0/0-0-0-0//.
Bar B4: 0-1-0-1/0-0-0-0/0-0-0-0/0-0-0-0//.

The patterns used for the knitting are reproduced in FIGS. 2A and 2B. Bars 3 and 4 are complementary. One of bars 3 and 4, for example bar B3, is threaded with monofilament yarns, for example 220 dtex poly(lactic acid), so as to give thickness and resilience to the three-dimensional knit. The other bar, for example bar B4, is threaded with multifilament yarns, for example 83.3 dtex poly(lactic acid), so as to give greater opacity between the faces: this opacity is due to the opening of the strands or filaments of the multifilament yarns in the spacer which creates a considerable visual filling coefficient.

Bars B3 and B4 can have an identical displacement and mesh at the same time, as represented in FIG. 2A, or, on the contrary, mesh shifted according to an alternative displacement as shown in FIG. 2B.

The knit is cleaned with methanol-ether and is sterilized by gamma-irradiation.

The knit is thermoset by placing it in an oven at approximately 90° C. for 1 to 5 min.

Example 4

Coating of the Knits of Examples 1 to 3

The knit obtained in Example 1, 2 or 3 is coated in a solution of porcine collagen at 0.8 w/v, by soaking it in the solution, spin-drying it and leaving it to dry under a laminar flow. This cycle of processes is repeated up to two times in order to obtain covering of the yarns.

The collagen used is porcine collagen type I, extracted from porcine dermis by solubilization at acidic pH or by digestion with pepsin, and purified by saline precipitations according to known techniques.

Dry collagen fibres obtained by precipitation of an acid solution of collagen by adding NaCl, and then washing and drying of the precipitate obtained with aqueous solutions of acetone having an increasing concentration of 80% to 100%, may be used.

At the end of the coating, the collagen deposited on the knit is crosslinked with glutaraldehyde at 0.5% w/v (aqueous solution of glutaraldehyde at 25%, w/v, sold by the company Fluka), at neutral pH (pH between 6.5 and 7.5), for 2 hours, and is then reduced with sodium borohydride. The reagents used are removed by washing the knit with several water baths.

The crosslinking of the collagen deposited on the knit can alternatively be carried out at the end of each coating cycle.

Figure 6:
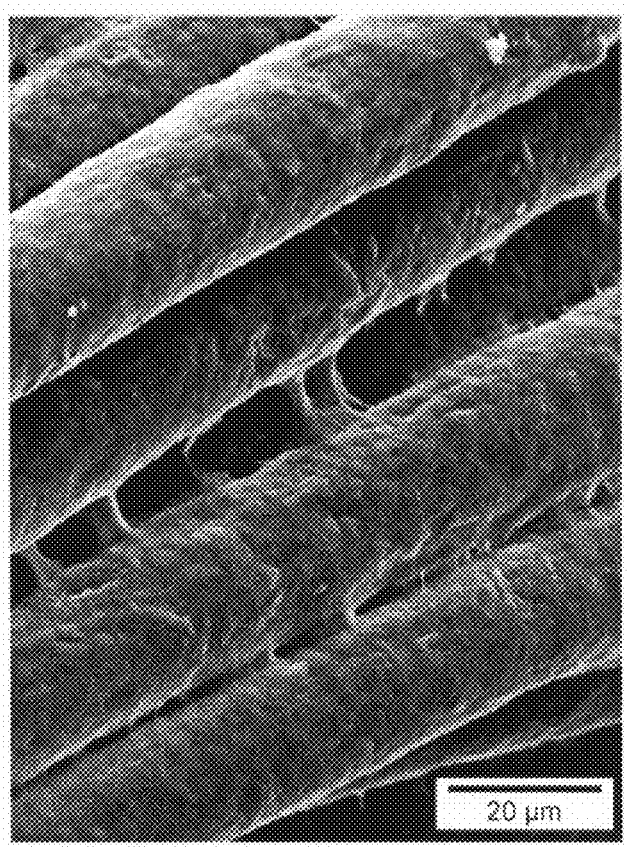
FIG. 6 is a scanning electron microscopy image (Hitachi S800 scanning electron microscope with image acquisition and analysis system) of the coated knit suitable for a support according to the present disclosure.

FIG. 6 is a scanning electron microscopy image of the coated knit obtained in Example 1.

Preparation of Glutaraldehyde-Crosslinked Collagen

Porcine collagen is solubilized in water at a final concentration of 1% w/v.

The collagen used is porcine collagen type I, extracted from porcine dermis by solubilization at acidic pH or by digestion with pepsin, and purified by saline precipitations according to known techniques.

Dry collagen fibres obtained by precipitation of an acid solution of collagen by adding NaCl, and then washing and drying the precipitate obtained with aqueous solutions of acetone having an increasing concentration of 80% to 100%, may be used.

The solution of collagen at 1% w/v is then neutralized by adding sodium phosphate at a final concentration of 20 mM. The final pH of the suspension was measured at between 6.5 and 7.5.

Glutaraldehyde (aqueous solution of glutaraldehyde at 25%, w/v, sold by the company Fluka) is then added to the suspension at a final concentration of 0.5% w/v. After two hours at ambient temperature, collagen fibres are recovered by filtration of the suspension through a nylon mesh. These fibres are then treated with sodium borohydride for at least two hours until the yellow coloration of the fibres has completely disappeared. The white fibres thus obtained are washed and neutralized at pH 6.5-7.5, and dried by removing the water with acetone. The acetone residues are then evaporated off.

Preparation of Oxidized Collagen

A solution of porcine collagen at 3% w/v is oxidized with periodic acid at a final concentration of 8 mM, at ambient temperature, according to Example 4 of U.S. Pat. No. 6,596,304.

Preparation of the Support:

A suspension of collagen is prepared by mixing the glutaraldehyde-crosslinked collagen and the oxidized collagen obtained above, at the following concentrations:

0.5 to 1.5% w/v of glutaraldehyde-crosslinked collagen,
0.2 to 1% w/v of oxidized collagen.

The collagen suspension thus obtained is then poured over the three-dimensional knit above so as to completely cover it and the whole is lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateaux, to +30° C. The lyophilization ends with secondary desiccation, at +30° C., for 1 to 24 hours. In embodiments, the vacuum at the end of secondary desiccation is between 0.005 and 0.2 mbar. The total lyophilization time is from 18 to 72 hours.

Figure 7:
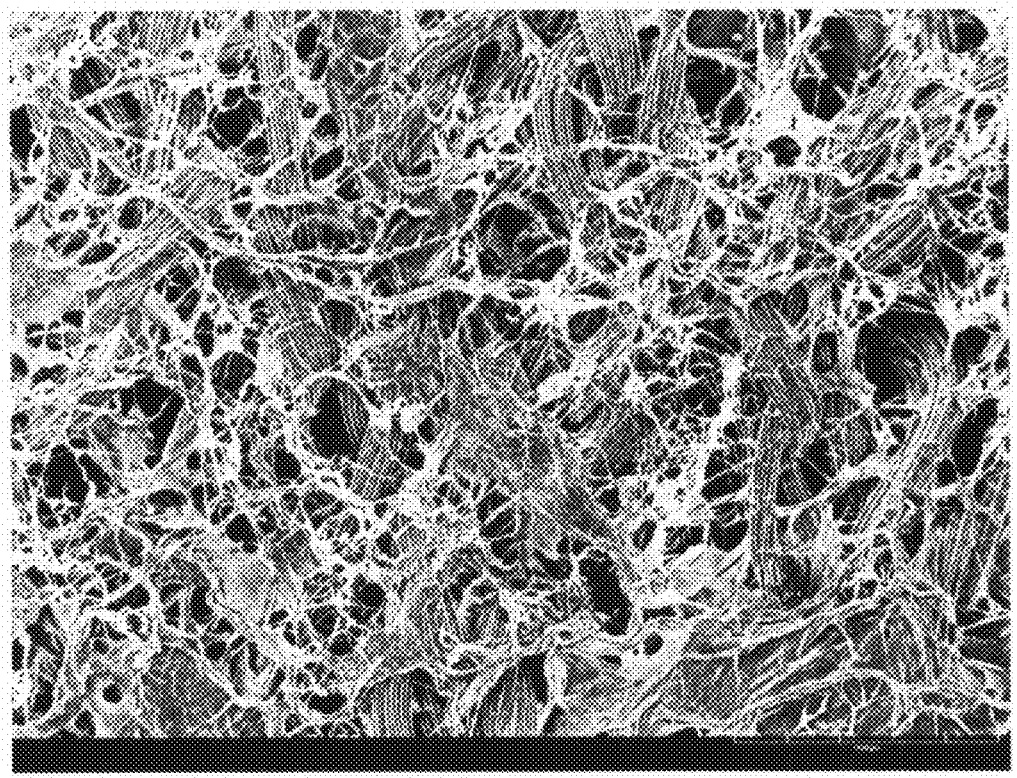
FIG. 7 is a rear view of an electron microscopy image (Hitachi S800 scanning electron microscope with image acquisition and analysis system) of a support according to the present disclosure, the three-dimensional knit being filled with the collagen matrix.
Figure 8:
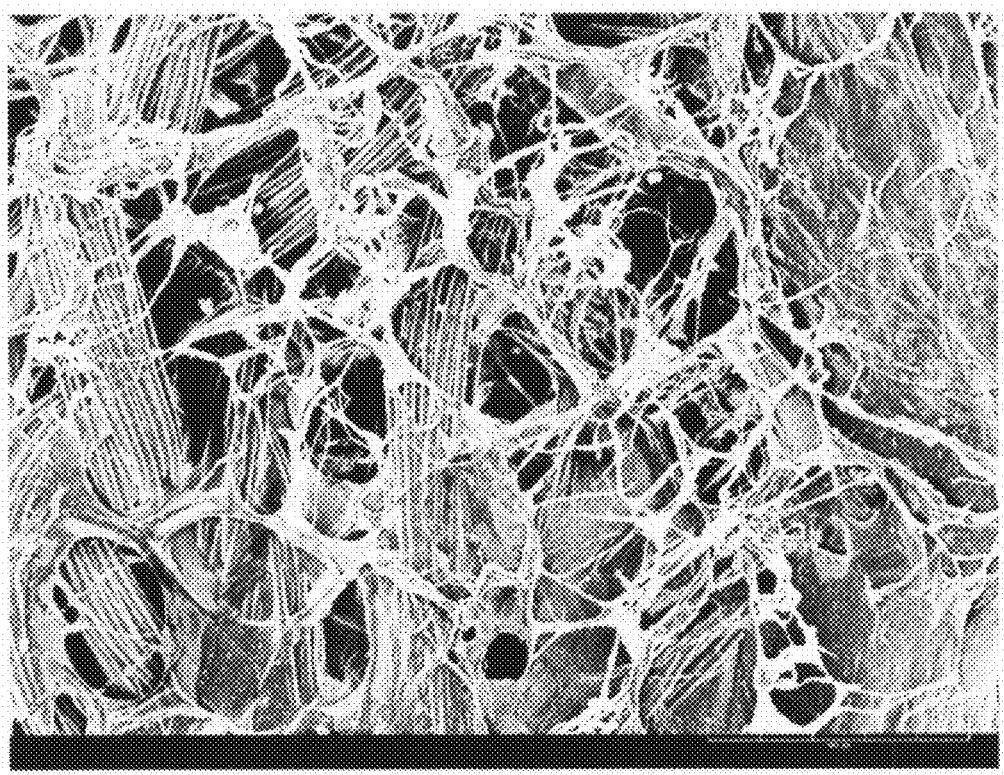
FIG. 8 is a rear view of an electron microscopy image (Hitachi S800 scanning electron microscope with image acquisition and analysis system) of a support according to the present disclosure, at a higher magnification than for FIG. 7, the three-dimensional knit being filled with the collagen matrix.

A support in which all the pores, i.e. those formed with the sponge and those of the three-dimensional knit, are at least partially interconnected, is obtained. Such interconnectivity is visible in the attached figures in which:

FIG. 7 is a rear view of a scanning electron microscopy image of the support obtained in the present example, with the three-dimensional knit filled with the collagen sponge matrix, FIG. 8 is a rear view, at a higher magnification, of a scanning electron microscopy image of the support obtained in the present example, with the three-dimensional knit filled with the collagen sponge matrix.

Application of a Film to One Face of the Support:

The support obtained above is subsequently coated with an oxidized collagen film as described in Example 2 of U.S. Pat. No. 6,391,939.

A concentrated sterile solution of PEG 4000 (polyethylene glycol having a molecular weight of 4000 D, for example sold by the company Fluka under the trade name PEG 4000) and glycerol is added to a solution of oxidized collagen (obtained by oxidation of porcine collagen) at 3% w/v, so as to obtain a final composition having a PEG 4000 concentration of 1% w/v and a glycerol concentration of 0.6% w/v. The pH of the solution is adjusted to 7.0 by adding a concentrated solution of sodium hydroxide. The volume of the solution is then adjusted with sterile water so as to obtain final concentrations of collagen, of PEG 4000 and of glycerol of 2.7% w/v, 0.9% w/v and 0.54% w/v, respectively. The solution is then spread out so as to form a thin sheet with a density of 0.133 g/cm$^2$ on a flat hydrophobic structure of polyvinyl chloride or polystyrene type. The surface is then exposed to a stream of sterile air at ambient temperature for just under one hour. The support obtained above is then applied carefully to the gelled sheet of oxidized collagen above. The whole is exposed to a stream of sterile air at ambient temperature until complete evaporation in about 18 hours.

Figure 9:
FIG. 9 is a view of an electron microscopy image (Hitachi S800 scanning electron microscope with image acquisition and analysis system) of a support according to the present disclosure coated with a collagen film.

FIG. 9 is a view of a scanning electron microscopy image of the support described above, coated with the collagen film.

Example 5

Preparation of Supports for Cell Culture Assays and Preparation of Supports for Tissue Engineering The knit in Example 1, in the form of pieces of 12.5×17.5 cm, is coated with a solution of oxidized porcine collagen at 0.8% w/v, by soaking it in the solution, spin-drying it and leaving it to dry under a laminar flow. This cycle of processes is repeated twice so as to obtain coating of the yarns. Pieces of coated knit, measuring 12.5×17.5 cm, are thus obtained.

A collagen suspension is prepared by mixing glutaraldehyde-crosslinked collagen and oxidized collagen so as to obtain the final concentration of each of the collagens of 5 g per litre:

5 g/l of glutaraldehyde-crosslinked collagen, on a dry weight basis,
5 g/l of oxidized collagen, on a dry weight basis.

The collagen suspension thus obtained is adjusted to pH 4.0 with dilute sodium hydroxide. It is then poured over the pieces of coated knit, measuring 12.5×17.5 cm, obtained above, so as to just be flush with the upper face, and the whole is lyophilized according to the following method: freezing is carried out as rapidly as possible, by decreasing the temperature of the product from +8° C. to −45° C. in less than 2 hours. Primary desiccation is initiated at −45° C., at a pressure of from 0.2 mbar. During this step, the temperature is gradually increased, with successive slopes and plateaux, to up to +30° C. The lyophilization ends with secondary desiccation, at +30° C. The total lyophilization time is one day.

A support according to the present disclosure is obtained, which can be cut up into discs 15 mm in diameter for the cell culture trials, or in the form of pieces measuring 5×7 cm$^2$ for the tissue engineering trials. These discs or pieces are sterilized by gamma-irradiation, at the minimum dose of 25 KGy.

Examples 6 to 10 which follow describe the seeding and the culturing of cells, carried out on supports according to the present disclosure as obtained in the present example.

The analytical techniques used in Examples 6 to 10 are described hereinafter:

Labelling of Cell Nuclei

The cells cultured on the supports according to the present disclosure are fixed for 20 minutes in a solution containing 4% of formaldehyde and 2% of sucrose. After rinsing for 5 minutes in PBS (phosphate buffered solution: 0.726 g/l Na$_2$HPO$_4$.7H$_2$O, 9 g/l NaCl, 0.21 g/l KH$_2$PO$_4$ [PBS Gibco, Invitrogen ref 20012-019]), the cell nuclei are labelled with Hoechst reagent (0.06% v/v in PBS buffer, molecular probes H3570). After two cycles of rinsing in PBS, the cells are observed under a confocal microscope using FITC ([09 shift free filter set, Zeiss ref 488009])/Rhodamine ([14 shift free filter set, Zeiss ref 488014])/DAPI ([02 shift free filter set, Zeiss ref 488002]) filters.

Viability Assay: "Live and Dead" Test

The viability of the cells cultured on the supports according to the present disclosure is verified by means of a "live and dead" assay ([molecular probes Ref L3224]), generally when the cells reach confluence/subconfluence. The seeded cells are rinsed twice with PBS buffer. The cells are labelled with 2 ml of PBS buffer containing Calcein AM 0.01% v/v, ethidium bromide 0.025% v/v and Hoechst reagent 0.03% v/v (counter-staining of nuclei [molecular probes Ref H3570]), for 30 minutes at +37° C. in an incubator. After two rinses with PBS, the supports are observed under a confocal microscope, using FITC/rhodamine/DAPI filters. Viability of the cells is expressed through a green colour, their morbidity through a red colour and their nuclei appear blue.

Immunolabelling

The phenotype of the cells is monitored by means of an immunolabelling assay. The cells cultured on the supports according to the present disclosure are fixed for 20 minutes with an aqueous solution containing 4% of formaldehyde and 2% of sucrose. After rinsing for 5 minutes in PBS buffer, the cells are treated with PBS buffer containing 0.5% of Tween 20, and then rinsed in PBS buffer and incubated in a rabbit serum. Without any other rinsing, the cells are labelled according to a procedure including two steps: first, contact with a primary antibody specific for SMCs (clone 1A4 mouse antihuman monoclonal antibody [Dako cytomation Ref M0851]) or urothelial cells, and a common secondary antibody ([Dako cytomation Ref E0464]). The visualisation is carried out with the ABC-AP Vectastin kit ([Vector Laboratory Ref AK 5000 series]) for 20 minutes. The nuclei are counterstained with Hoechst reagent and the immunolabelled cells are observed under a confocal microscope.

Example 6

Culture of Supports with Porcine Bladder Smooth Muscle Cells (SMCs)

1) Protocol for Extraction of Smooth Muscle Cells (SMCs) from Fresh Porcine Bladders The porcine bladders are received fresh and conserved in sterile PBS buffer. The samples are taken within 24 h.

The bladders are opened up along their length using a sterile scalpel, and then spread out on a sterile blister dressing, with the muscle face upwards.

A sheet of peritoneal cells is removed, allowing free access to the muscle sheet.

The muscle tissue is separated from the adipose base, and then chopped up with a scalpel in a sterile petri dish.

The tissues thus recovered are placed in a sterile 50 ml centrifuge tube filled with collagenase Ia at 1 mg/ml (collagenase type I [Invitrogen Ref 17100-017]), and then left to incubate at 37° C. for 40 min on a roller mixer.

The tubes are centrifuged at 600 rpm for 5 min, at ambient temperature, and the supernatant is then drawn off and replaced with fresh complete culture medium (DMEM Glutamax [Invitrogen ref 31966-021], 10% foetal calf serum [Invitrogen ref 10270-106], 1% antibiotic [penicillin-streptomycin solution stabilized/Sigma, Ref P4458]).

The tissues are mixed and a few drops of medium containing the cell suspension are placed at the bottom of a petri dish, scarified beforehand in order to increase tissue attachment. The tissues thus adherent are left to incubate at 37° C. for 30 min in an air/$CO_2$ incubator.

The petri dish is then made up to 10 ml with complete medium (DMEM Glutamax [Invitrogen ref 31966-021], 10% foetal calf serum [Invitrogen ref 10270-106], 1% antibiotic [penicillin-streptomycin solution stabilized/Sigma, Ref P4458]), the cells are then left to incubate in an air/$CO_2$ incubator and the media are changed every 48 hours.

The cells thus obtained are frozen at −80° C. in a proportion of $10^6$ cells/ml of complete DMEM medium, in 1 ml aliquots (DMEM Glutamax [Invitrogen ref 31966-021], 10% foetal calf serum [Invitrogen ref 10270-106], 5% dimethyl sulphoxide (DMSO, [Sigma Ref 8418])).

2) Cell Culture Before Seeding of the Support

The cell cultures of the cells obtained in point 1) are carried out by taking an appropriate medium in 25 or 75 $cm^2$ cell culture flasks.

Thus, these smooth muscle cells (SMCs) are cultured in DMEM medium (DMEM Glutamax medium [Invitrogen ref 31966-021]) supplemented with 10% of foetal calf serum (Invitrogen ref 10270-106) and 1% antibiotics (penicillin-streptomycin solution stabilized [Sigma, Ref P4458]), in uncoated flasks.

3) Cell Culture Method

The cells are thawed for 3 min at +37° C. The 1 ml aliquot of solution mentioned above, containing the cells, is mixed with 10 ml of the appropriate medium (DMEM Glutamax [Invitrogen ref 31966-021], 10% foetal calf serum [Invitrogen ref 10270-106], 1% antibiotics [penicillin-streptomycin solution stabilized/Sigma, Ref P4458]) and centrifuged for 5 minutes at 1500 rpm, in order to remove the DMSO (DMSO, [Sigma Ref 8418]). The supernatant is removed and the cells are suspended in 10 ml of complete DMEM medium (DMEM Glutamax [Invitrogen ref 31966-021], 10% foetal calf serum [Invitrogen ref 10270-106], 1% antibiotics [penicillin-streptomycin solution stabilized/Sigma, Ref P4458]) and seeded into a 25 $cm^2$ cell culture flask.

The complete DMEM medium is replaced every 2-3 days with a fresh medium (10 ml).

At confluence, the cells are rinsed twice with a solution of PBS (phosphate buffered solution: 0.726 g/l $Na_2HPO_4.7H_2O$, 9 g/l NaCl, 0.21 g/l $KH_2PO_4$ [PBS Gibco, Invitrogen ref 20012-019]) and detached with trypsin, (Invitrogen ref 15090-046) for 3 minutes for the SMCs. The cells collected are suspended in a fresh complete DMEM medium, and centrifuged at 1500 rpm for 5 minutes. The supernatant is removed, and the cells are suspended in fresh complete DMEM medium and distributed into three culture flasks.

The cells are monitored by optical microscopy. The cell viability is verified by means of a "live and dead" assay (as described in Example 5) under a confocal microscope and the conservation of the cell phenotype is verified by means of immunochemical assays (as described in Example 5), after fixing and by confocal micrscopy.

4) Seeding of the Supports

The supports according to the present disclosure, in the form of the discs obtained in Example 5, are rinsed twice in the PBS buffer (phosphate buffered solution: 0.726 g/l $Na_2HPO_4.7H_2O$, 9 g/l NaCl, 0.21 g/l $KH_2PO_4$, [PBS Gibco, Invitrogen ref 20012-019]) at +37° C., in an incubator with 5% $CO_2$, for one hour. The cells are seeded into the supports, at a rate of 100 000 cells/support 15 mm in diameter.

After they have been seeded, the supports are placed in an incubator for 30 minutes at +37° C. in order to facilitate the adhesion of the cells. 1 ml of the appropriate culture medium (DMEM Glutamax [Invitrogen ref 31966-021], 10% foetal calf serum [Invitrogen ref 10270-106], 1% antibiotics [penicillin-streptomycin solution stabilized/Sigma, Ref P4458] is then added to each support, before leaving them in the incubator at +37° C.

Over the course of the incubation, the complete DMEM medium is renewed every two days with fresh complete DMEM medium.

5) Culturing of the Seeded Supports

The SMCs, seeded onto the supports according to the present disclosure as described in point 4) above, are incubated at +37° C. for 1 hour and 4, 8 and 15 days, with the medium being changed every two days.

Before they are observed, the cells are fixed in formaldehyde for 20 minutes and stained with EBH (ethidium bromide ethidium (0.025% v/v ethidium bromide ([molecular probes Ref L3224]) their nuclei being counterstained with 0.03% v/v Hoechst reagent ([molecular probes Ref H3570]), as described in Example 5.

Verification of the conservation of the SMC phenotype by labelling of alpha-actin ((clone 1A4 mouse antihuman monoclonal antibody [Dako cytomation Ref M0851]) and secondary antibody ([Dako cytomation Ref E0464), visualisations carried out with the ABC-AP Vectastain kit ([Vector Laboratory Ref AK 5000 series])) is carried out during the exponential proliferation phase, as described in Example 5, before confluence is reached.

It is verified, under the microscope, that the SMCs show good adhesion and a satisfactory proliferation rate on the supports according to the present disclosure. Three-dimensional colonisation of the supports is observed from the 4th day of incubation onwards. After 15 days of culture, the SMCs appear to be almost confluent on the supports according to the present disclosure. The SMCs have clearly spread out and proliferated on the yarns of the knit and in the open pores of the supports.

Conservation of the phenotype is confirmed after 8 days of culture by virtue of the fact that the cytoplasm of the SMCs is red in colour, following alpha-actin labelling of the SMCs. Thus, the physiochemical properties of the collagen sponge matrix of the supports according to the present disclosure has no effect on the phenotype of the SMCs.

Example 7

Culturing of Supports with Porcine Bladder Urothelial Cells

1) Protocol for Extraction of Urothelial Cells from Fresh Porcine Bladders

The bladders are received fresh and conserved in sterile PBS buffer. The samples are taken within 24 h.

The bladders are opened up along their length using a sterile scalpel and then spread out on a sterile blister, with the bladder lumen upwards. The urothelium (the first cell sheets) is removed using sterile forceps and scissors, and then chopped up with a scalpel in a sterile petri dish. The tissues thus recovered are placed in a sterile 50 ml centrifuge tube filled with collagenase Ia at 1 mg/ml, and then left to incubate at 37° C. for 40 min on a roller mixer.

The tubes are centrifuged at 600 rpm for 5 min, at ambient temperature, and then the supernatant is drawn up and replaced with fresh complete culture medium (medium for keratinocyte-SFM, growth factor-supplemented: defined keratinocyte medium [Gibco Invitrogen, ref 10784-015], defined keratinocyte-SFM [Gibco Invitrogen, ref 10785-012]).

The tissues are mixed and a few drops of medium containing the cell suspension are placed on the bottom of a petri dish, scarified beforehand in order to increase tissue attachment and coated with porcine collagen at 0.2%. The tissues thus adherent are left to incubate at 37° C. for 30 min in an air/$CO_2$ incubator.

The petri dish containing the adherent tissues is then made up with 10 ml of complete medium (medium for keratinocyte-SFM, growth factor-supplemented: defined keratinocyte medium [Gibco Invitrogen, ref 10784-015], defined keratinocyte-SFM [Gibco Invitrogen, ref 10785-012]) and the cells are then left to incubate in an air/$CO_2$ incubator and the media are changed every 48 hours.

The cells thus obtained are frozen at −80° C. at a rate of $10^6$ cells/ml of complete medium (medium for keratinocyte-SFM, growth factor-supplemented: defined keratinocyte medium [Gibco Invitrogen, ref 10784-015], defined keratinocyte-SFM [Gibco Invitrogen, ref 10785-012]), in 1 ml aliquots.

2) Cell Culture Before Seeding of hte Supports

The cell cultures are prepared by taking an appropriate medium in 25 or 75 $cm^2$ cell culture flasks.

The urothelial cells obtained in point 1) of the present example are cultured in defined medium for keratinocytes (defined keratinocyte medium [Gibco Invitrogen, ref 10784-015], defined Keratinocyte-SFM [Gibco Invitrogen, ref 10785-012]), in flasks coated with 0.15% of oxidized porcine collagen type I.

3) Cell Culture Method

The cells obtained in point 1) of the present example are thawed for 3 min at +37° C. The 1 ml solution of medium (defined keratinocyte medium [Gibco Invitrogen, ref 10784-015], defined keratinocyte-SFM [Gibco Invitrogen, ref 10785-012]) containing the cells is mixed with 10 ml of an appropriate medium and centrifuged for 5 minutes at 1500 rpm, in order to remove the DMSO. The supernatant is removed and the cells are suspended in 10 ml of medium and seeded into a 25 $cm^2$ cell culture flask.

The medium is replaced every 2-3 days with a fresh medium (10 ml).

At confluence, the cells are rinsed twice with a solution of PBS and detached with trypsin (Invitrogen ref 15090-046) for 10 minutes. The cells collected are suspended in fresh medium containing 10% of foetal calf serum, and centrifuged at 1500 rpm for 5 minutes. The supernatant is removed, and the cells are suspended in a fresh medium and distributed into three culture flasks.

The cells are monitored by optical microscopy. The viability of the cells is verified by means of a "live and dead" assay under a confocal microscope and the conservation of the phenotype of the cells is verified by means of immunochemical assays, after fixing and by confocal microscopy, as described in Example 5.

4) Seeding of the Supports

The supports according to the present disclosure, in the form of the discs obtained in Example 5, are rinsed twice in the PBS buffer (phosphate buffered solution: 0.726 g/l $Na_2HPO_4.7H_2O$, 9 g/l NaCl, 0.21 g/l $KH_2PO_4$, [PBS Gibco, Invitrogen ref 20012-019]) at +37° C., in an incubator with 5% $CO_2$, for one hour. The cells are seeded into the supports, at a rate of 100 000 cells/support 15 mm in diameter.

After they have been seeded, the supports are placed in an incubator at 37° C. for 30 minutes in order to facilitate adhesion of the cells. 1 ml of the appropriate culture medium is then added to each support, before leaving them in the incubator at +37° C.

Over the course of the incubation, the medium is renewed every two or three days with an appropriate fresh complete medium (defined keratinocyte medium [Gibco Invitrogen, ref 10784-015], defined keratinocyte-SFM [Gibco Invitrogen, ref 10785-012]).

5) Culturing of the Seeded Supports

The urothelial cells, seeded onto the supports according to the present disclosure as described in point 4) of the present example, are incubated at +37° C. for 1 hour and 5 and 7 days, with the medium being changed every two days.

Before they are observed, the cells are fixed in formaldehyde for 20 minutes and stained with EBH, their nucleus being counterstained with Hoechst reagent (as described in Example 5). Observation under a confocal microscope is then carried out.

After proliferation for five days, the urothelial cells are immunolabelled with anti-pancytokeratin antibodies, their nuclei being counterstained with Hoechst reagent.

It is verified, under the microscope, that the urothelial cells show quite good adhesion after one hour, on the supports according to the present disclosure. The urothelial cells seeded into the supports according to the present disclosure form morphological arrangements in clusters and adopt pentagonal shapes characteristic of the urothelium (Southgate et al., Laboratory Investigation, 1994).

After five days of culture, the positive immunolabelling of the urothelial cells with the anti-pancytokeratin antibodies indicates that the phenotype of the cells has been conserved.

Example 8

Culturing of Supports with Stem Cells, Mesenchymal Cells, Extracted from Porcine Bone Marrow 1) Extraction of Stem Cells from Bone Marrow Ten ml of fresh porcine bone marrow are received. The samples are taken within 24 h.

Ten ml of porcine bone marrow are diluted at a 1:2 ratio in sterile PBS buffer.

Five ml of diluted bone marrow are mixed carefully with 3 ml of histopaque ([Sigma Ref H8889]) in sterile centrifuge tubes, and then centrifuged at 2000 rpm for 20 min at 20° C. with the brake released. The purpose of this is to separate the mononuclear cells from the rest of the bone marrow constituents. The releasing of the brake is an essential parameter.

Three phases are obtained. The intermediate phase is removed and the media are made up to 20 ml with sterile PBS/EDTA buffer at 4° C.

After centrifugation at 4500 rpm for 5 min at 20° C. and removal of the supernatant, the cells are resuspended in DMEM medium (DMEM Glutamax [Invitrogen ref 31966-021]) at a concentration of $2\times10^6$ cells/ml.

3 ml of cell suspension thus obtained are seeded into a petri dish and the whole is left to incubate for 12 hours in an air/$CO_2$ incubator.

The supernatant containing the non-adherent cells is removed and replaced with complete medium, without antibiotics (DMEM Glutamax [Invitrogen ref 31966-021], 10% foetal calf serum [Invitrogen ref 10270-106]) and the cells are left to proliferate to confluence, with the media being changed every 48 hours.

2) Culturing of the Supports with Stem Cells, Mesenchymal Cells, Extracted from Porcine Bone Marrow The stem cells extracted from porcine bone marrow according to point 1) of the present example are cultured in DMEM supplemented with 10% foetal calf serum and antibiotics (5% of penicillin-streptomycin antibiotics) (DMEM Glutamax [Invitrogen ref 31966-021], 10% foetal calf serum [Invitrogen ref 10270-106], 1% antibiotics [penicillin-streptomycin solution stabilized/Sigma, Ref P4458]). This culture medium, which is free of growth factors, allows the cells to proliferate and also to be maintained in an undifferentiated state. They adopt an SMC-type morphology when they are undifferentiated and are in the proliferation phase.

The stem cells are then seeded, at a rate of 100 000 or 200 000 cells per support 14 mm in diameter as obtained in Example 5. The cells are incubated at +37° C. for 4 days, with the medium being changed every two days.

Before they were observed, the cells were fixed in formaldehyde for 20 minutes and then stained with EBH, their nucleus being counterstained with Hoechst reagent, as described in Example 5. The stem cells were observed under a confocal microscope.

It is verified under the microscope that the stem cells proliferate correctly in the supports according to the present disclosure.

In order to be sure that the stem cells still have a differentiation potential, these cells were converted to mature cells of osteoblast type.

The stem cells are left to proliferate for 7 days, in the SMC culture medium. The stem cells are then differentiated, by replacing the culture medium with a new medium, DMEM enriched with 10% foetal calf serum, 100 mM of ascorbate-2-phosphate, 100 nM (nanomolar) of dexamethasone and 10 mM of β-glycerophosphate. The medium is renewed every two days and the cells are incubated for 4 weeks in order for them to become completely differentiated.

After 4 weeks of incubation, the cells are immunolabelled with markers specific for mature osteoblasts (osteocalcin, Cbfa1, collagen type I) and are observed under a confocal microscope.

It is verified under the microscope that the cells seeded into the supports according to the present disclosure are very strongly labelled for collagen type I and Cbfa1 and, to a lesser extent, for osteocalcin. The cells are correctly differentiated into mature osteoblasts, throughout the thickness of the supports according to the present disclosure. They have kept the differentiation potential.

Example 9

Culturing of SMCs in Supports Measuring 5×7 $cm^2$ for Tissue Engineering/Long Culture Time Rectangular samples, measuring 5×7 $cm^2$, of the support according to the present disclosure obtained in Example 5 are inserted into sterile petri dishes 12 cm in diameter, and then immersed in 20 ml of sterile PBS buffer and left to incubate overnight in an air/$CO_2$ incubator.

The SMCs are cultured in complete DMEM medium (DMEM Glutamax [Invitrogen ref 31966-021], 10% foetal calf serum [Invitrogen ref 10270-106], 1% antibiotics [penicillin-streptomycin solution stabilized/Sigma, Ref P4458]).

After removal of the culture medium, the cells cultured in T75 culture flasks are rinsed with PBS buffer (phosphate buffered solution: 0.726 g/l $Na_2HPO_4.7H_2O$, 9 g/l NaCl, 0.21 g/l $KH_2PO_4$, [PBS Gibco, Invitrogen ref 20012-019]), and then detached using 5 ml of trypsin ([Invitrogen ref 15090-046]) by incubation for 3 min in an air/$CO_2$ incubator. The cells thus detached are mixed with 15 ml of complete medium, and two samples of 20 µl are taken therefrom in order to count the cells, before they are centrifuged for 5 min at 4500 rpm.

The supernatant is removed and the cells are resuspended in fresh complete medium at a concentration of $4\times10^5$ cells/ml.

After rinsing of the samples, the cells are seeded onto the collagen sponge part of the support according to the present disclosure at a rate of $2\times10^6$ cells concentrated in 5 ml, deposited carefully onto the entire support. After one hour of adhesion in an air/$CO_2$ incubator, the medium is made up with 20 ml of fresh complete medium.

The whole is left to incubate in an air/$CO_2$ incubator and the media are changed every 48 hours for the first 7 days and then every 24 hours on the following days, until the support according to the present disclosure is used as an implant.

After 4 days of proliferation, a "live and dead" assay is carried out on the supports in order to verify the cell viability.

After 8 and 15 days of proliferation, a verification of the phenotype is carried out by means of immunochemical labelling ((clone 1A4 mouse antihuman monoclonal antibody [Dako cytomation Ref M0851]), secondary antibody ([Dako cytomation Ref E0464]), visualisation carried out with the ABC-AP Vectastain kit ([Vector Laboratory Ref AK 5000 series]), in situ, of the cells as described in Example 5.

Example 10

Culturing of SMCs in Supports Measuring 5×7 cm² for Tissue Engineering/Short Culture Time Rectangular samples, measuring 5×7 cm², of the support according to the present disclosure obtained in Example 5 are inserted into sterile petri dishes 12 cm in diameter, and then immersed in 20 ml of sterile PBS buffer (phosphate buffered solution: 0.726 g/l $Na_2HPO_4.7H_2O$, 9 g/l NaCl, 0.21 g/l $KH_2PO_4$, [PBS Gibco, Invitrogen ref 20012-019]), and left to incubate overnight in an air/$CO_2$ incubator.

The smooth muscle cells (SMCs) are cultured in complete DMEM medium (DMEM Glutamax [Invitrogen ref 31966-021], 10% foetal calf serum [Invitrogen ref 10270-106], 1% antibiotics [penicillin-streptomycin solution stabilized [Sigma Ref P4458]).

After removal of the culture medium, the cells cultured in T75 culture flasks are rinsed with PBS buffer and then detached using 5 ml of trypsin ([Invitrogen Ref 15090-046]) by incubation for 3 min in an air/$CO_2$ incubator. The cells thus detached are mixed with 15 ml of complete medium, and two samples of 20 µl are taken therefrom in order to count the cells, before they are centrifuged for 5 min at 4500 rpm.

The supernatant is removed and the cells are resuspended in fresh medium at a concentration of $2 \times 10^6$ cells/ml.

After rinsing of the samples, the cells are seeded onto the collagen sponge part of the supports according to the present disclosure at a rate of $10^7$ cells concentrated in 5 ml of complete DMEM medium, deposited carefully onto the entire support. After 1 hour of adhesion in an air/$CO_2$ incubator, the medium is made up with 20 ml of fresh complete DMEM medium.

The whole is left to incubate in an air/$CO_2$ incubator for 48 hours before the supports thus cellularized are used as implants.

A sample is used for the verification tests and the immunochemical labellings before the supports are used as implants.

It will be understood that various modifications may be made to the embodiments disclosed herein. Therefore, the above description should not be construed as limiting, but merely as exemplifications of preferred embodiments. Those skilled in art will envision other modifications within the scope and spirit of the claims appended hereto.

The invention claimed is:

1. A cell culture or tissue engineering support comprising:
   (i) a porous matrix based on a collagen sponge which defines first pores,
   wherein said collagen comprises a mixture of at least one collagen which undergoes slow bioresorption in vivo and at least one collagen which undergoes rapid bioresorption in vivo; and
   (ii) a porous three-dimensional knit which defines second pores;
   wherein said porous matrix fills said three-dimensional knit and all the first and second pores are interconnected with one another.

2. A support according to claim 1, wherein said porous matrix is bioresorbable.

3. A support according to claim 1, wherein said three-dimensional knit is bioresorbable.

4. A support according to claim 1, wherein the collagen which undergoes slow bioresorption in vivo is selected from the group consisting of glutaraldehyde-crosslinked collagen, bifunctional or trifunctional glycidyl ethers, carbodiimides, acyl azides and mixtures thereof.

5. A support according to claim 1, wherein the collagen which undergoes rapid bioresorption in vivo is selected from the group consisting of oxidized collagen, glutaraldehyde-crosslinked collagen, bifunctional or trifunctional glycidyl ethers, carbodiimides, acyl azides, collagen crosslinked by UV irradiation or by heat treatment, and mixtures thereof.

6. A support according to claim 1, wherein the collagen forming said sponge is a mixture of oxidized collagen and glutaraldehyde-crosslinked collagen.

7. A support according to claim 1, wherein said three-dimensional knit consists of monofilament and/or multifilament yarns made of bioresorbable material which has an in vivo degradation time ranging from approximately 3 months to 2 years.

8. A support according to claim 7, wherein said bioresorbable material is selected from the group consisting of poly(lactic acid) (PLA), poly(glycolic acid) (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyethers, copolymers thereof and mixtures thereof.

9. A support according to claim 7, wherein at least a part of the yarns constituting said three-dimensional knit are coated with a bioresorbable coating.

10. A support according to claim 9, wherein said coating comprises collagen, chitosan, polysaccharides or mixtures thereof.

11. A support according to claim 9, wherein said coating is made of collagen.

12. A support according to claim 1, wherein said second pores have an average diameter ranging from 1 to 5 mm.

13. A support according to claim 1, wherein said knit has a two-dimensional porosity of less than or equal to 20%.

14. A support according to claim 1, wherein said knit has a three-dimensional porosity of greater than or equal to 90%.

15. A support according to claim 1, wherein said three-dimensional knit has a thickness ranging from approximately 2 mm to 6 mm.

16. A support according to claim 1, wherein said three-dimensional knit comprises a first face and a second face, said first face and said second face being opposite and separated from one another by the thickness of said knit, said first face and said second face being connected to one another by a spacer made of monofilament yarns, multifilament yarns or a combination of monofilament yarns and multifilament yarns.

17. A support according to claim 16, wherein said spacer is made of monofilament yarns.

18. A support according to claim 17, wherein said monofilament yarns which make up said spacer consist of yarns made of material which undergoes slow bioresorption.

19. A support according to claim 18, wherein said monofilament yarns which make up said spacer are made of poly(lactic acid).

20. A support according to claim 16, wherein said first and second faces of the knit are made of monofilament yarns, multifilament yarns or a combination of monofilament and multifilament yarns.

21. A support according to claim 16, wherein the monofilament or multifilament yarns used to prepare the first and second faces and the spacer of the three-dimensional knit are chosen from yarns made of material which undergoes slow bioresorption, yarns made of material which undergoes rapid bioresorption, and mixtures thereof.

22. A support according to claim 21, wherein the yarns made of material which undergoes slow bioresorption are made of poly(lactic acid).

23. A support according to claim 21, wherein the yarns made of material which undergoes rapid bioresorption selected from the group consisting of poly(glycolic acid) yarns, oxidized cellulose yarns, poly(lactic acid) yarns partially degraded by a treatment such as repeat cycles of gamma-irradiation at doses of greater than or equal to 25 kGy, and mixtures thereof.

24. A support according to claim 21, wherein said first and second faces are made of a mixture of multifilament yarns made of material which undergoes slow bioresorption and of multifilament yarns made of material which undergoes rapid bioresorption.

25. A support according to claim 16, wherein said first and second faces are made of poly(lactic acid) multifilament yarns.

26. A support according to claim 1, wherein said knit is isoelastic.

27. A support according to claim 1, wherein said knit has a mechanical strength in the longitudinal direction, measured according to ISO standard 13934-1, ranging from 50 to 300N.

28. A support according to claim 27, wherein said knit has a mechanical strength in the longitudinal direction, measured according to ISO standard 13934-1, ranging from 100 to 250 N.

29. A support according to claim 28, wherein said knit has a mechanical strength in the transverse direction, measured according to ISO standard 13934-1, ranging from 75 to 200 N.

30. A support according to claim 1, wherein said knit has a mechanical strength in the transverse direction, measured according to ISO standard 13934-1, ranging from 50 to 300 N.

31. A support according to claim 1, wherein said knit has an elongation at 50 N in the longitudinal direction, measured according to ISO standard 13934-1, ranging from 10% to 50%.

32. A support according to claim 1, wherein said knit has an elongation at 50 N in the transverse direction, measured according to ISO standard 13934-1, ranging from 10% to 50%.

33. A support according to claim 1, further comprising one or more active compounds selected from the group consisting of antiseptics, anti-inflammatories, growth factors, polysaccharides extracellular matrix proteins, and mixtures thereof.

34. A support according to claim 1, wherein the support is seeded with live cells.

35. A support according to claim 34, wherein the cells are selected from the group consisting of striated muscle cells, smooth muscle cells, endothelial cells, epithelial cells, mesothelial cells, fibroblasts, myofibroblasts, stem cells of striated muscle cells, stem cells of smooth muscle cells, stem cells of endothelial cells, stem cells of epithelial cells, stem cells of mesothelial cells, stem cells of fibroblasts, stem cells of myofibroblasts, and combinations thereof.

36. A support according to claim 34, wherein the cells are smooth muscle cells.

37. A support according to claim 34, wherein the cells are urethelial cells.

38. A cell culture or tissue engineering support comprising:
(i) a porous matrix based on a collagen sponge which defines first pores
(ii) a porous three-dimensional knit which defines second pores,
wherein said porous matrix fills said three-dimensional knit and all the first and second pores are interconnected with one another, and said cell culture or tissue engineering support has at least two faces; and
(iii) a bioresorbable film on at least one of the faces,
wherein said bioresorbable film comprises at least one collagen.

39. A support according to claim 38, wherein said film comprises oxidized collagen, polyethylene glycol and glycerol.

40. A support according to claim 34, wherein said collagen sponge is seeded with muscle cells and said bioresorbable film is seeded with endothelial or epithelial cells.

41. A support according to claim 34, wherein said collagen sponge is seeded with striated muscle cells and said bioresorbable film is seeded with mesothelial cells.

42. A support according to claim 34, wherein said collagen sponge is seeded with smooth muscle cells and said bioresorbable film is seeded with urothelial cells.

* * * * *